(12) United States Patent
Warnack et al.

(10) Patent No.: US 8,292,913 B2
(45) Date of Patent: Oct. 23, 2012

(54) METHOD OF REDUCING RIGIDITY OF ANGIOPLASTY BALLOON SECTIONS

(75) Inventors: Boris Warnack, Rangendingen (DE); Judith Hartwig, Grosselfingen (DE); Silke Pschibl, Rangendingen (DE); Travis Richard Yribarren, San Mateo, CA (US); Randolf Von Oepen, Los Altos Hills, CA (US); Thomas Rieth, Hirrlingen (DE); Lorcan Coffey, Tuebingen (DE); Arik Zucker, Zurich (CH)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 13/152,081

(22) Filed: Jun. 2, 2011

(65) Prior Publication Data

US 2011/0284498 A1 Nov. 24, 2011

Related U.S. Application Data

(62) Division of application No. 11/455,382, filed on Jun. 19, 2006, now Pat. No. 7,967,836.

(60) Provisional application No. 60/692,920, filed on Jun. 17, 2005.

(51) Int. Cl.
*A61M 29/00* (2006.01)
(52) U.S. Cl. ............... 606/194; 604/96.01; 604/103.05; 604/103.07
(58) Field of Classification Search ............ 604/103.05, 604/103.07, 96.01; 606/194
See application file for complete search history.

(56) References Cited

U.S. PATENT DOCUMENTS

| | | | | |
|---|---|---|---|---|
| 4,531,943 A | * | 7/1985 | Van Tassel et al. | 604/523 |
| 4,776,337 A | * | 10/1988 | Palmaz | 623/1.11 |
| 4,782,834 A | | 11/1988 | Maguire et al. | |
| 4,950,232 A | * | 8/1990 | Ruzicka et al. | 604/43 |
| 4,963,133 A | | 10/1990 | Whipple | |
| RE33,561 E | | 3/1991 | Levy | |
| 5,049,132 A | * | 9/1991 | Shaffer et al. | 604/101.02 |
| 5,087,244 A | * | 2/1992 | Wolinsky et al. | 604/509 |
| 5,180,364 A | * | 1/1993 | Ginsburg | 604/510 |

(Continued)

FOREIGN PATENT DOCUMENTS

EP 1537892 6/2005

(Continued)

OTHER PUBLICATIONS

U.S. Appl. No. 11/455,382, May 23, 2011 Issue Fee payment.

(Continued)

*Primary Examiner* — Christopher D Koharski
*Assistant Examiner* — Scott Medway
(74) *Attorney, Agent, or Firm* — Baker Botts LLP

(57) ABSTRACT

A dilatation balloon is fabricated according to a process that forms cavities and indentations in the balloon and/or catheter sections. A length of tubing is axially elongated and radially expanded in a form to provide the requisite biaxial orientation and strength. Then, an excimer laser or another type of laser or mechanical material removal tool is used to remove the polymeric material, virtually without thermal effects. Cavities in the sleeve sections of the balloon are defined and if desired, indentations in the cone sections are defined. Material removal, particularly near the balloon sleeves enables a thinner, more flexible bonding area between the catheter shaft and the balloon. Further, the indentations along the cone sections enables tighter wrapping of the balloon for a reduced delivery profile. Rigidity near the sleeves is reduced for better maneuverability of the catheter in tortuous passageways.

19 Claims, 6 Drawing Sheets

U.S. PATENT DOCUMENTS

| | | | |
|---|---|---|---|
| 5,254,091 A * | 10/1993 | Aliahmad et al. | 604/103.06 |
| 5,306,250 A * | 4/1994 | March et al. | 604/104 |
| 5,318,587 A | 6/1994 | Davey | |
| 5,370,617 A * | 12/1994 | Sahota | 604/102.02 |
| 5,378,237 A * | 1/1995 | Boussignac et al. | 604/103.01 |
| 5,443,495 A * | 8/1995 | Buscemi et al. | 623/1.21 |
| 5,480,383 A * | 1/1996 | Bagaoisan et al. | 604/102.02 |
| 5,496,292 A * | 3/1996 | Burnham | 604/526 |
| 5,533,988 A * | 7/1996 | Dickerson et al. | 604/523 |
| 5,545,132 A | 8/1996 | Fagan et al. | |
| 5,554,121 A * | 9/1996 | Ainsworth et al. | 604/103.1 |
| 5,562,620 A * | 10/1996 | Klein et al. | 604/103.01 |
| 5,571,086 A * | 11/1996 | Kaplan et al. | 604/96.01 |
| 5,591,129 A * | 1/1997 | Shoup et al. | 604/103.1 |
| 5,599,306 A * | 2/1997 | Klein et al. | 604/103.01 |
| 5,637,113 A * | 6/1997 | Tartaglia et al. | 623/1.42 |
| 5,733,301 A * | 3/1998 | Forman | 606/192 |
| 5,749,852 A * | 5/1998 | Schwab et al. | 604/103.01 |
| 5,762,637 A * | 6/1998 | Berg et al. | 604/264 |
| 5,779,698 A * | 7/1998 | Clayman et al. | 606/39 |
| 5,797,878 A * | 8/1998 | Bleam | 604/196 |
| 5,826,588 A | 10/1998 | Forman | |
| 6,024,722 A * | 2/2000 | Rau et al. | 604/96.01 |
| 6,048,332 A * | 4/2000 | Duffy et al. | 604/103.08 |
| 6,048,338 A | 4/2000 | Larson et al. | |
| 6,110,192 A | 8/2000 | Ravenscroft et al. | |
| 6,280,411 B1 * | 8/2001 | Lennox | 604/103.05 |
| 6,364,894 B1 * | 4/2002 | Healy et al. | 606/194 |
| 6,368,301 B1 * | 4/2002 | Hamilton et al. | 604/103 |
| 6,491,711 B1 | 12/2002 | Durcan | |
| 6,613,066 B1 * | 9/2003 | Fukaya et al. | 606/192 |
| 6,623,504 B2 * | 9/2003 | Vrba et al. | 606/192 |
| 6,695,830 B2 * | 2/2004 | Vigil et al. | 604/509 |
| 6,702,802 B1 | 3/2004 | Hancock et al. | |
| 6,881,201 B1 | 4/2005 | Duchamp | |
| 7,048,714 B2 * | 5/2006 | Richter | 604/103.02 |
| 7,201,763 B2 * | 4/2007 | Heidner | 606/194 |
| 7,306,616 B2 * | 12/2007 | Eidenschink et al. | 606/194 |
| 7,527,606 B2 | 5/2009 | Oepen | |
| 7,625,353 B2 | 12/2009 | Grandt et al. | |
| 7,637,935 B2 | 12/2009 | Pappas et al. | |
| 7,967,836 B2 | 6/2011 | Warnack et al. | |
| 2003/0078613 A1 | 4/2003 | Heidner | |
| 2004/0116956 A1 | 6/2004 | Duchamp et al. | |
| 2004/0225318 A1 | 11/2004 | Eidenschink et al. | |

FOREIGN PATENT DOCUMENTS

WO    WO00/57816    10/2000

OTHER PUBLICATIONS

U.S. Appl. No. 11/455,382, Apr. 15, 2011 Notice of Allowance.
U.S. Appl. No. 11/455,382, Nov. 29, 2010 Supplemental Amendment.
U.S. Appl. No. 11/455,382, Sep. 7, 2010 Amendment and Request for Continued.
U.S. Appl. No. 11/455,382, Apr. 6, 2010 Final Office Action.
U.S. Appl. No. 11/455,382, Jan. 8, 2010 Response to Non-Final Office Action.
U.S. Appl. No. 11/455,382, Jul. 8, 2009 Non-Final Office Action.
U.S. Appl. No. 11/455,382, Jun. 5, 2009 Amendment and Request for Continued Examination (RCE).
U.S. Appl. No. 11/455,382, Mar. 5, 2009 Final Office Action.
U.S. Appl. No. 11/455,382, Dec. 11, 2008 Response to Non-Final Office Action.
U.S. Appl. No. 11/455,382, Sep. 5, 2008 Non-Final Office Action.

* cited by examiner

METHOD OF REDUCING RIGIDITY OF ANGIOPLASTY BALLOON SECTIONS

CROSS-REFERENCE TO RELATED APPLICATION

This application is a Divisional of application Ser. No. 11/455,382, filed Jun. 19, 2006 now U.S. Pat. No. 7,967,836, which claims the benefit of U.S. Provisional Patent Application Ser. No. 60/692,920, filed Jun. 17, 2005, each of which are incorporated herein in their entirety by reference thereto.

FIELD OF THE INVENTION

The present invention relates generally to dilatation balloon catheters and systems used for expansion against an obstruction within a body vessel or channel, or to deliver devices such as, but not limited to, intravascular stents and therapeutic agents to sites within vascular or tubular channel systems of the body. Particularly, the invention relates to a dilatation balloon catheter and system having an improved dilatation balloon. The dilatation balloon has improved pliability, trackability and maneuverability in the passages of the vascular system.

BACKGROUND OF THE INVENTION

The present invention relates to dilatation balloon catheters employed in applications such as percutaneous transluminal angioplasty (PTA) and percutaneous transluminal coronary angioplasty (PTCA) procedures, and more particularly to enhancements to such catheters and their dilatation balloons for improved maneuverability in smaller and more tortuous passages of the vascular system.

Dilatation balloon catheters are well known for their utility in treating the build-up of plaque and other occlusions in blood vessels. Typically a catheter is used to carry a dilatation balloon to a treatment site, where fluid under pressure is supplied to the balloon, to expand the balloon against an obstruction. Additionally, the expansion of the balloon may deploy a stent device in the treatment area.

The dilatation balloon is typically mounted along the distal portion, e.g., distal end region, of the catheter and coaxially surrounds the catheter shaft. Upon expansion of the dilatation balloon, the main body portion or medial section, of the balloon, sometimes referred to as the working portion, increases to define a diameter which is substantially larger than the diameter of the catheter shaft. Proximal and distal sleeves or stems of the balloon have diameters substantially equal to the diameter of the catheter. Proximal and distal tapered sections, or cones, join the medial region to the proximal and distal shafts, respectively. Each cone diverges in the direction toward the medial region. Bonds between the balloon and catheter form a fluid tight seal to facilitate dilatation of the balloon by introduction of a fluid under pressure.

Along with body tissue compatibility, primary attributes considered in the design and fabrication of dilatation balloons are strength and pliability. A higher hoop strength or burst pressure generally reduces the risk of accidental rupture of a balloon during dilatation, although this is also dependent on the characteristics of the vessel lesion.

Pliability refers to formability into different shapes, rather than elasticity. In particular, when the balloon is an uninflated configuration, the dilatation balloon is evacuated, flattened and generally wrapped circumferentially about the catheter distal region. Thin, pliable dilatation balloon walls facilitate a tighter wrap that minimizes the combined diameter of the catheter and balloon during delivery. Furthermore, pliable balloon walls enhance the catheter "trackability" in the distal region, i.e. the capability to bend in conforming to the curvature in vascular passages.

One method of forming a strong and pliable dilatation balloon of polyethyleneterephthalate (PET) is disclosed in U.S. Pat. No. Re. 33,561 (Levy). A tubing of PET is heated at least to its second order transition temperature, then drawn to at least triple its original length to axially orient the tubing. The axially orientated tubing is then radially expanded within a cylindrical form, to a diameter at least triple the original diameter of the tubing. The form defines the aforementioned main body, shafts and cones, and the resulting balloon has a burst pressure of greater than 200 psi.

Such balloons generally have a gradient in wall thickness along the cones. In particular, dilatation balloons with an expansion diameter in the range of 3.0-4.0 mm tend to have a wall thickness along the main body in the range of 0.0004-0.0008 inches (0.010-0.020 mm). Near the main body, the cones have approximately the same wall thickness. However, the wall thickness diverges in the direction away from the main body, until the wall thickness near each shaft is in the range of 0.001-0.0025 inches (0.025-0.063 mm). Smaller dilatation balloons (1.5-2.5 mm) exhibit the same divergence in the cone walls, i.e. from 0.0004-0.0008 inches near the main body to 0.0008-0.0015 inches (0.02-0.04 mm) near the associated shaft or stem.

The increased wall thickness near the stems does not contribute to balloon hoop strength, which is determined by the wall thickness along the balloon medial region. Thicker walls near the stems reduce maneuverability of the balloon and catheter. The dilatation balloon cannot be as tightly wrapped, meaning its delivery profile is larger, limiting the capacity of the catheter and balloon for treating occlusions in smaller vessels.

U.S. Pat. No. 4,963,133 (Noddin) discloses an alternative approach to forming a PET dilatation balloon, in which a length of PET tubing is heated locally at opposite ends and subjected to axial drawing, to form two "necked down" portions which eventually become the opposite ends of the completed balloon. The necked down tubing is simultaneously axially drawn and radially expanded with a gas. The degree to which the tubing ends are necked down is said to provide control over the ultimate wall thickness along the tapered walls (or cones), so that the wall thickness can be equal to or less than the wall thickness along the main body. This approach, however, is said to result in a comparatively low burst pressure, only about 8 atmospheres, or about 118 psi.

Typically, the balloon is secured to an elongate member of the catheter shaft. In this manner, the proximal and distal sleeves of the balloon is secured for example, heat welded to a catheter shaft. The bonded area of the balloon often gets stiffer and larger in diameter after bonding to the catheter shaft. This is partly due to material accumulation, and to crystallization of the polymer material of the balloon.

Therefore, it is an object of the present invention to provide a dilatation balloon having a high burst pressure, high hoop strength, good folding characteristics, and good trackability.

A further object is to provide a balloon with portions of the balloon wall selectively thinned to enable a tighter wrapping of the balloon circumferentially about a catheter distal end region, for a reduced profile during balloon delivery.

Yet another object is to provide a process for selectively removing material from a balloon catheter and its dilatation balloon, to enhance catheter trackability and maneuverability without crystallization, embrittlement or other thermal degradation of material. This selective removal of material may be achieved through the use of an excimer laser. This selective removal of material may also be achieved through the use of a phemto-second laser, or any other laser source that is capable of material removal. This selective removal of material may also be achieved through the use of a mechanical process such as drilling, milling, blasting, etching, or grinding.

SUMMARY OF THE INVENTION

The purpose and advantages of the present invention will be set forth in and apparent from the description that follows, as well as will be learned from the practice of the invention. Additional advantages of the invention will be realized and attained by the methods and systems particularly pointed out in the written description and claims hereof, as well as from the appending drawings.

To achieve these and other advantages, and in accordance with the purpose of the invention, as embodied herein and broadly described, the invention includes a dilatation balloon having a tapered region such as proximal and distal cone sections and a working or medial section disposed therebetween. The medical balloon further includes a mounting region such as proximal and distal sleeve sections disposed proximate the proximal and distal cones, respectively.

The mounting region is adapted for fluid tight bonding to a catheter or other delivery device. The dilatation balloon medial or working region is substantially larger in diameter than the mounting region and is adapted to engage tissue at a treatment site responsive to expansion of the dilatation balloon, or to expand a stent device within a treatment site. The balloon tapered region or cone sections between the working or medial region and the mounting region diverges in the direction from the mounting region toward the working region. This section may also be stepped, have a non-circular cross-section, or be otherwise reduced in diameter from the working region to the mounting region.

In one aspect of the invention, the expandable balloon includes at least one cavity disposed along the proximal or distal sleeve sections. In another aspect of the invention, the balloon includes at least one indentation along the length of proximal or distal cone sections of the balloon and indentations in the cone sections of the balloon. In this manner, the balloon can be fabricated according to a process that includes: directing a laser beam onto a biaxially oriented balloon at a selected location along an exterior surface of the balloon to ablatively remove material therefrom. Alternatively, a variety of known techniques other than ablation, for example, milling, grinding and other suitable known techniques can be used to form the cavities or indentations in accordance with the present invention.

Further, the at least one cavity and/or the at least one indentation can include a plurality of cavities and/or plurality of indentations randomly dispersed along the balloon sections or dispersed in a specific pattern along the balloon sections.

In one embodiment, the wall thickness of the tapered portion having undergone the ablative process is substantially equal to the nominal wall thickness of the medial working section of the balloon. Alternatively the tapered sections may have thicknesses greater or less than the nominal wall thickness of the balloon. In either event, the indentations are configured to increase balloon maneuverability and pliability by reducing balloon wall stiffness near the mounting sections, and allows a tighter wrapping of the balloon for a reduced delivery profile.

Thus in accordance with the present invention, polymeric material is removed from catheters and dilatation balloons by selective excimer laser ablation, phemto-second laser milling, the use of any other laser source that enables material ablation, or mechanical processes to reduce dilatation balloon wrapping profiles and increase flexibility in the balloon and catheter for accommodating curvature in arterial passageways and other body cavities. The improvements are achieved while maintaining a balloon burst pressure above 8 atm.

It is to be understood that both the foregoing general description and the following detailed description are exemplary and are intended to provide further explanation of the invention claimed.

The accompanying drawings, which are incorporated in and constitute part of this specification, are included to illustrate and provide further understanding of the method and system of the invention. Together with the description, the drawings serve to explain the principles of the invention.

BRIEF DESCRIPTION OF THE DRAWINGS

For a further appreciation of the above and other advantages, reference is made to the following detailed description and to the drawings, in which.

DETAILED DESCRIPTION OF THE PREFERRED EMBODIMENTS

Figure 1:
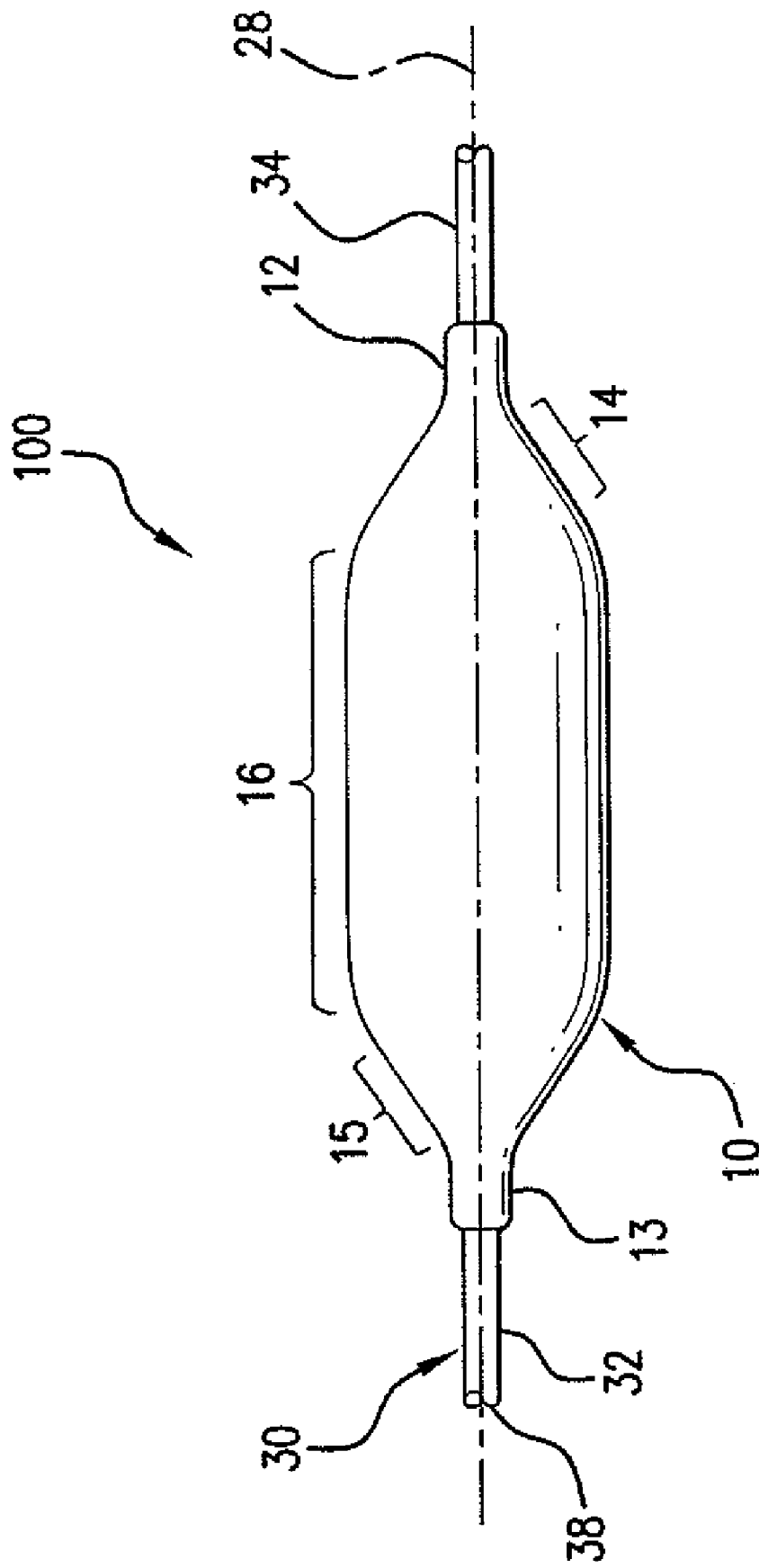
FIG. 1 is a partial plan view of the distal end of the dilation balloon catheter in accordance with the present invention.

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

In one aspect of the present invention, a medical device is provided. The medical device generally comprises an elongated shaft member having a proximal end and a distal end. The elongated shaft member further includes a guidewire lumen and an inflation lumen extending along a length thereof. Further, an expandable member such as a balloon is disposed proximate the distal end of the shaft. The expandable member is in fluid communication with the inflation lumen extending along the elongated shaft member.

Referring now to FIG. 1, the expandable medical device 100 in accordance with the present invention is shown. In accordance with the invention, the medical device 100 includes a catheter shaft 30 having a proximal end 32 and a distal end 34. An inflation lumen 38 is disposed within the elongate catheter shaft 30. Further, the catheter shaft 30 includes a guidewire lumen (not shown) extending along a length of the catheter shaft 30. In one embodiment, the guidewire lumen can be disposed within the elongate shaft 30 between the proximal end 32 and the distal end 34 to define an over-the-wire catheter. Alternatively, the guidewire lumen can be disposed at least in the proximal section of catheter shaft 30 to define a rapid exchange catheter system, if desired. Further, the guidewire lumen can be configured to define a coaxial or a side-by-side arrangement with catheter shaft 30.

A balloon 10 is disposed proximate the distal end 34 of the shaft 30. The inflation lumen 38 is in fluid communication with an interior of the balloon and the proximal end 32 of the shaft 30. The shaft 30 further includes a hub (not shown) disposed on the proximal end 32. The hub preferably includes two lumens, a first lumen in communication with the guidewire lumen and the second in communication with the inflation lumen. A central axis extends through the balloon 10, wherein the sections of the balloon as described above are radially disposed about the axis, thereby forming a balloon having generally cylindrical and conical shapes. The balloon 10 is sealed in a fluid tight manner about the catheter shaft 30 and in fluid communication with the inflation lumen 38 of the catheter shaft 30. When fluid is introduced into the inflation lumen, the balloon expands about a central axis of the shaft 30.

In accordance with the invention, a medical device such as an endoprosthesis (not shown) can be disposed radially about the balloon 10, wherein expansion of the balloon permits deployment of the endoprosthesis. Exemplary endoprosthesis' are shown and described in co-pending U.S. patent application Ser. No. 10/430,636 entitled "Endoprosthesis For Controlled Contraction and Expansion" and U.S. patent application Ser. No. 10/430,644 entitled "Endoprosthesis Having Foot Extensions" the entireties of which are herein incorporated by reference.

The catheter shaft 30 may be constructed from a variety of suitable materials or a combination of suitable materials. For example, the shaft 30 can be constructed of polymer materials including nylon, polyimide, Pebax or metallic materials including stainless steel, nitinol and other alloys. Further, the proximal section of the catheter shaft may formed from a material different than the distal section of the catheter depending on the intended application of the medical device 100. For example, the proximal section of the catheter can be formed from a variety of materials including but not limited to metal, metal alloy, carbon, carbon reinforced materials, metal reinforced polymers, boron fiber reinforced materials, glass reinforced materials, aramid fiber reinforced materials, ceramic, composite, Kevlar, or polymer. The distal section of the shaft 30 may be formed of but not limited to polyamide, PEEK, PTFE, PVDF, PEBAX®, polyimide, polyester, polyurethane, liquid crystal polymer, or polyethylene of various suitable densities.

A suitable example of a catheter shaft construction is shown and described in co-pending U.S. Patent Applications entitled "Catheter Having Coil-Defined Guidewire Passage" having application Ser. No. 11/136,251 filed May 24, 2005; "Catheter Having First and Second Guidewire Tubes And Overlapping Stiffening Members" having application Ser. No. 11/136,640 filed May 24, 2005 and U.S. Provisional Patent Applications entitled "Multiple Lumen Catheter and Method of Making Same" having application Ser. No. 60/684,143, filed May 24, 2005; "Catheter Having Plurality of Stiffening Members" having application Ser. No. 60/684,135 filed May 24, 2005. The entire contents of each of which are incorporated herein by reference.

In accordance with the invention, and as shown in FIG. 1, balloon 10 includes proximal cone section 15, a distal cone section 14 and a medial section extending therebetween 16. The balloon further includes a proximal sleeve section 13 and a distal sleeve section 12 disposed proximate proximal and distal cone sections, respectively. The balloon is preferably made of polymeric material such as nylon or Pebax. Alternatively, however, other materials can be used as desired.

The balloon 10 is fabricated using techniques known in the art. For example and not limitation, the balloon may be fabricated by this process including the steps of a) axially drawing a length of polymeric tubing to substantially elongate a length of the tubing while heating the tubing to a temperature above its second order transition temperature, to axially orient the tubing; b) radially expanding the tubing to substantially increase the diameter along at least a portion of the tubing length while maintaining the tubing above the second order transition temperature, to radially orient the tubing, thus to form a biaxially oriented balloon with a medial section having a nominal diameter and a nominal wall thickness, proximal and distal end mounting sections and proximal and distal tapered sections between the medial section and the proximal and distal end mounting sections respectively; c) allowing the biaxially oriented balloon to cool below the second order transition temperature. However, other suitable methods of forming a balloon can be used, as would be known in the art.

Figure 2:
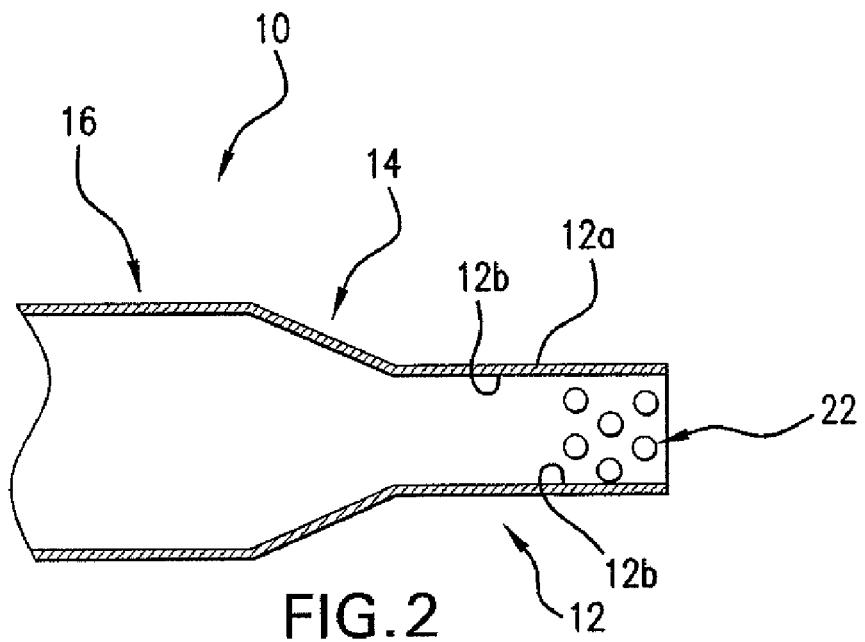
FIG. 2 is a partial plan view of one embodiment of a balloon having at least one cavity in accordance with the invention.

In accordance with one aspect of the invention, and as depicted in FIG. 2, the balloon proximal or distal sleeve sections 12, 13 includes at least one cavity 22 formed in the wall of the sleeve sections. Preferably, the at least one cavity 22 is a plurality of cavities formed in the wall of at least one of the proximal or distal sleeve sections 12, 13.

The wall of the sleeve includes a first surface 12a and a second surface 12b. For example, the first surface can be the outer surface of the sleeve section and the second surface can be the inner surface of the sleeve section. The at least one cavity includes a cut extending through at least one of the first or second surfaces of the wall of the sleeve section. For example, the cavity can include a cut which extends through both the first and second sleeve sections. In this manner, a hole or opening is defined through the wall of the sleeve section. Alternatively, however, the cavity can include a cut which only extends through one of the first or second surfaces. For example and not limitation, the cut can extend through an outer surface of the wall of the sleeve section but not penetrate through the inner surface of the wall of the sleeve section. In this manner, a pitted area is defined in the wall of the sleeve section. The pitted area preferably has a sufficient depth extending in the wall of the sleeve to collect flowing polymer material from the balloon during bonding to a catheter shaft, as will be discussed below.

The cavity 22 defined in the wall of the distal or proximal sleeve sections is formed by the removal of material from the sleeve section. A variety of techniques can be used for removing the material from the proximal or distal sleeve section to define the cavity. For example but not limitation, the cavity can be formed by at least one technique including laser ablation, mechanical grinding, milling, blasting, drilling, chemical or mechanical etching and any combination thereof. However, any suitable method can be used to remove the material, as would be known in the art. Alternatively, for example, the balloon including at least one cavity in the wall of the sleeve section can be formed by use of a mold or other device, such as a die.

In accordance with one embodiment of the invention, as shown in FIG. 2, the sleeve section 12 includes a plurality of cavities 22 that are scattered or randomly disposed about a length of the sleeve section. In this regard, the length could be the circumferential length of the sleeve section, the longitudinal length of the sleeve section or both. Alternatively, the plurality of cavities can be disposed in a predetermined pattern along the circumferential or longitudinal length of the sleeve section, as shown in FIGS. 3 and 4.

Figure 3:
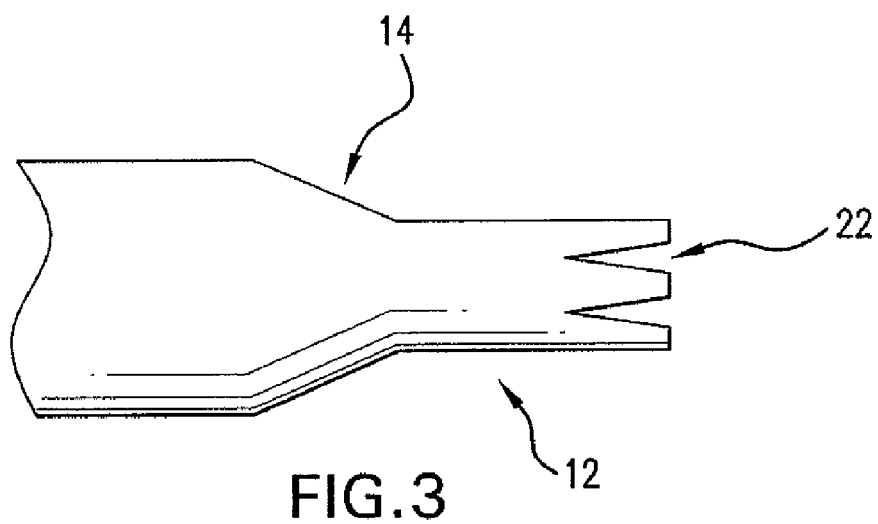
FIG. 3 is a partial plan view of a balloon having at least one cavity extending from the edge of the balloon sleeve in accordance with the invention.

In another embodiment of the invention, as depicted in FIG. 3, the at least one cavity includes at least one cut extending from an edge of the proximal or distal sleeve section along the longitudinal length thereof. Further and as shown in FIG. 3, a plurality of cuts can be disposed about the circumferential length of the sleeve section to define a plurality of cavities.

Figure 4:
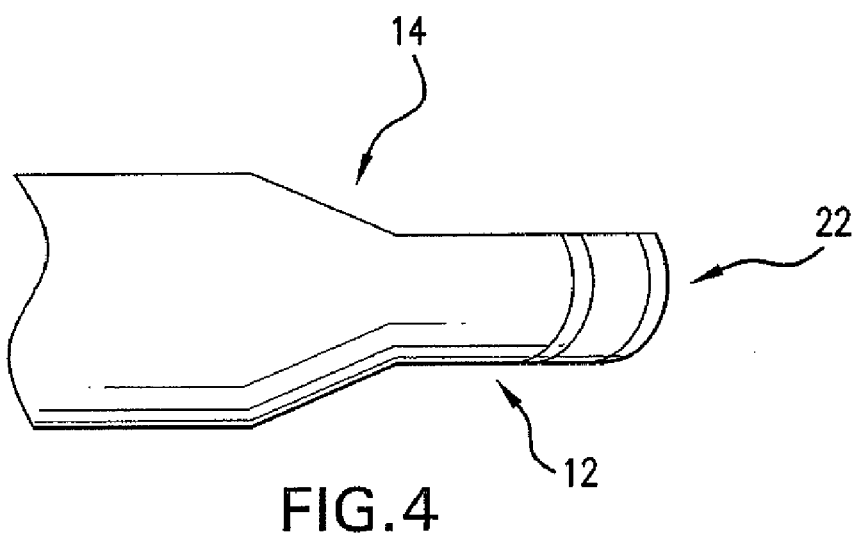
FIG. 4 is a partial plan view of balloon having a spirally shaped cavity along a length of the balloon sleeve in accordance with the invention.

In yet another embodiment of the invention, the cavity can be configured to define a spiral or helical cut circumferentially about the proximal or distal sleeve section, as shown in FIG. 4. In this manner, preferably, the cavity extends through only one of the first or second surfaces of the wall of the sleeve section. In this manner, the cavity defines a pitted area in the wall of the sleeve section.

In accordance with various embodiments of the invention, as depicted in FIGS. 2, 3 and 4, a cavity can be defined as a circular shaped structure, a triangular shaped structure, or a spiral or helical shaped structure. Alternatively, the at least one cavity can be configured to define other suitable shapes including but not limited to a star shape, polygonal shape or sinusoidal shape for example but not limitation.

As discussed the at least one cavity can include a plurality of cavities, the depth of the cavities may be constant or varied, as desired. For example, the plurality of cavities can include cavities having the same or different depths relative to one another and relative to the thickness of the wall of the proximal or sleeve sections. In this regard, the depth of the cavity defined in the wall of the proximal or distal sleeve section should be sufficient to receive molten polymer material from the sleeve section during bonding to a catheter shaft. In this regard, the proximal and/or distal sleeve sections are configured to define a bonding area which provides a reduced bonding profile when bonded to the catheter shaft.

Figure 5:
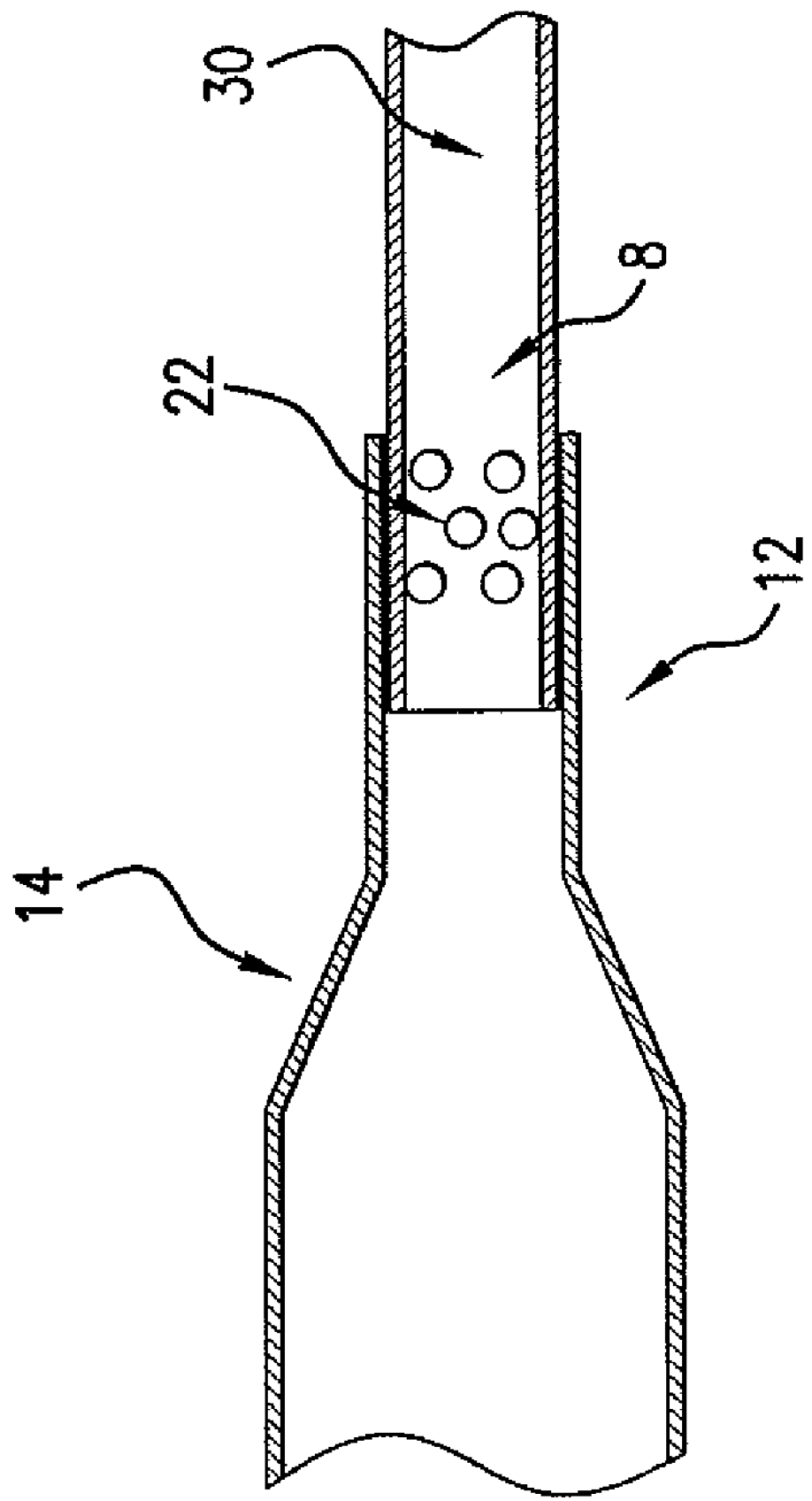
FIG. 5 is the balloon of FIG. 2 bonded to a catheter shaft in accordance with the invention.

Accordingly, in yet another embodiment of the present invention a catheter having a reduced bonding profile is provided, as depicted in FIG. 5. The catheter includes an elongate shaft member 30 having a proximal section and a distal section and a length therebetween. The balloon 10 in accordance with the invention is bonded to the distal section of the catheter. During the bonding process, the polymeric material of the balloon becomes molten and flows into the cavities defined in the wall of the proximal and distal sleeve sections. In this aspect of the invention, the reduced bonding profile 8 is defined by the molten polymeric material from the proximal and/or distal sleeve section flowing into the at least one cavity. Accordingly, a thinner and more flexible bond is achieved due to the reduction in the amount of material at the bonding area. In one embodiment of the invention, the cavities are entirely filled with the flowing polymer such that the cavities are no longer visible after the balloon is bonded to the shaft.

Figure 6:
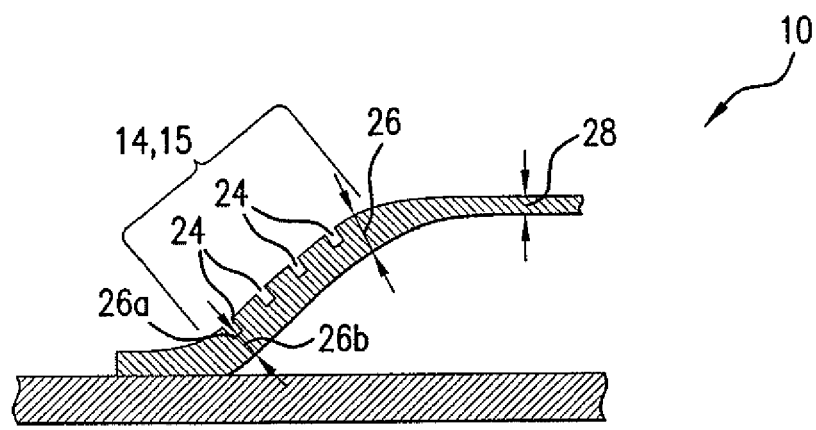
FIG. 6 is a partial cross-sectional view of the distal end of the dilation balloon described herein, wherein indentations have been formed within a portion of the balloon in accordance with the present invention.

In another aspect of the invention, referring now to FIG. 6, there is shown a partial cross-sectional view of the balloon 10, wherein the balloon 10 is shown in an expanded state. The balloon further comprises at least one indentation 24 disposed along a length of the proximal and/or distal cone sections 14, 15. The proximal and distal cone sections 14, 15 each include a wall having a first thickness 26. The medial or working section of the balloon includes a wall having a second thickness 28. The at least one indentation 24 includes a depth 26a extending into the wall or thickness 26 of the proximal and/or distal cone sections 14, 15 to define a third reduced thickness 26b along a section of the proximal or distal cone sections.

In one embodiment, the reduced thickness 26b defined by the indentation in the wall of the cone section is not less than the thickness of the wall of the medial section 28 of the balloon, as schematically shown in FIG. 6. For example and not limitation, the reduced thickness 26b defined by the depth 26a of the indentation 24 is substantially equal to the thickness 28 of the wall of the medial section 16.

The wall thickness 26 of the cone section 15 is shown to be approximately twice the wall thickness 28 of the medial or working section 16 of the balloon. Although certain wall thicknesses are shown and described herein, they should not be considered limiting in any manner and are merely provided for exemplary purposes. In this example, the depth of the indentations 24, i.e. the distance from the bottom of the indentation to the inner surface of the cone section 15, is substantially equal to the wall thickness 28 of the medial or working section 16. It shall be understood that this is an example, and the relative wall thicknesses of these sections may vary. The dimensions for the indentations 24 may also vary due to manufacturing tolerances.

As with the at least one cavity described above, the at least one indentation is formed by at least one technique selected from the group consisting of laser ablation, mechanical grinding, milling, blasting, drilling, chemical or mechanical etching and any combination thereof. However, other suitable techniques can be used.

In this aspect of the invention, the balloon 10 in accordance with the present invention can be folded to a smaller effective diameter than balloons not manufactured according to the teachings of the present invention. The indentations 24 are configured to reduce the stiffness of the cone sections 14, 15. This reduction in stiffness results in a more pliable balloon that can be wrapped tighter about the diameter of the catheter, which leads to a lower crossing profile. The indentations 24 also reduce the average wall thickness of the cone sections 14, 15. Therefore, the medical device 100 in accordance with the present invention is capable of being inserted into smaller body vessels and tubular channels than similar medical devices.

Further, the medical device 100 illustrated in the partial cross-sectional view of FIG. 1 exhibits better trackability than presently available medical devices. The improved trackability is due to the indentations which are formed on the cone sections 14, 15 of the balloon 10, as shown in FIG. 6. The indentations 24 reduce the stiffness of the balloon 10. The reduced stiffness leads to improved flexibility of the balloon 10 and therefore the medical device 100. The increased flexibility allows the medical device 10 to conform more easily to the tortuous vascular passages that it passes, or tracks, through. Additionally, since the average stiffness of the affected balloon sections are lower, they will conform more easily to the vessel during expansion, which has benefit in terms of reducing trauma to the body vessels or tubular channels. Further, the reduced profile bonds achieved by the at least one cavity defined in the proximal and/or distal sections of the sleeve sections contributes to the advantages of the catheter such as flexibility and lower profile, as discussed above.

Figures 7, 8:
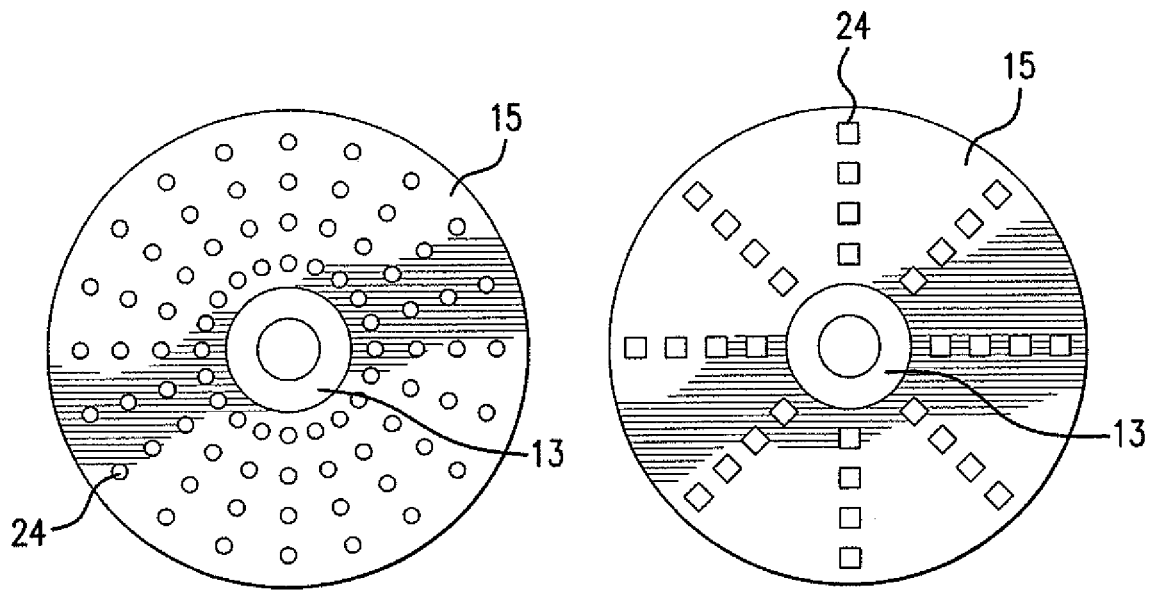
FIGS. 7 and 8 are end views of exemplary embodiments of dilation balloons fabricated in accordance with the present invention.

In accordance with the present invention, referring now to FIG. 7, there is shown an end view of an exemplary embodiment of proximal cone section 15 including a plurality of indentations 24 formed along a length thereof. As shown in FIG. 7, the indentations 24 are represented as having a generally circular shape. The depth and diameter of these indentations 24 may be constant or varied relative another indentation and relative to the wall of the cone section. Additionally, although the pattern of indentations 24 formed on the cone sections 14, 15 depicted in FIG. 7 is semi-uniform, this should not be considered limiting in any manner. It is contemplated that the indentations 24 may be disposed on the proximal or distal cone sections 14, 15 utilizing random distribution or specific patterns. For example, and as depicted in FIG. 8, an alternative embodiment includes a plurality of indentations 24 disposed in a specific and predetermined pattern in the wall of the cone section 15. For the purpose of illustration and not limitation, the indentations 24 are patterned in a uniformly spaced series disposed in a radial direction.

Further, as shown in FIG. 8, the indentations 24 in accordance with the alternative embodiment have a generally square shape. As previously described, the indentations 24 may be formed having other geometric features, such as polygonal shapes including triangular, circular, pentagonal, star-shaped, or other similar geometries, or any combination thereof. Further, the indentations can be formed to have a linear or sinusoidal shape, if desired, including but not limited to spiral path, linear path, circular rings, or disposed in completely randomized locations. Further still, the indentations 24 disposed on the cone sections of the balloon can include one or more geometric patterns that may be in accordance with the present invention.

As discussed, the indentations 24 or the cavities 22 described herein in accordance with the present invention can be formed in the balloon 10 using a variety of processes. In one embodiment, it is contemplated that a laser source may be used to ablate material in the desired areas to form the indentations 24 or cavities 2.

Figure 9:
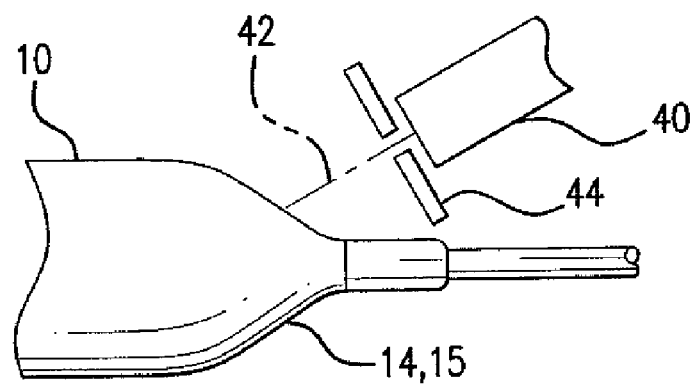
FIG. 9 illustrates a method of forming indentations using an excimer laser and a mask element.
Figure 10:
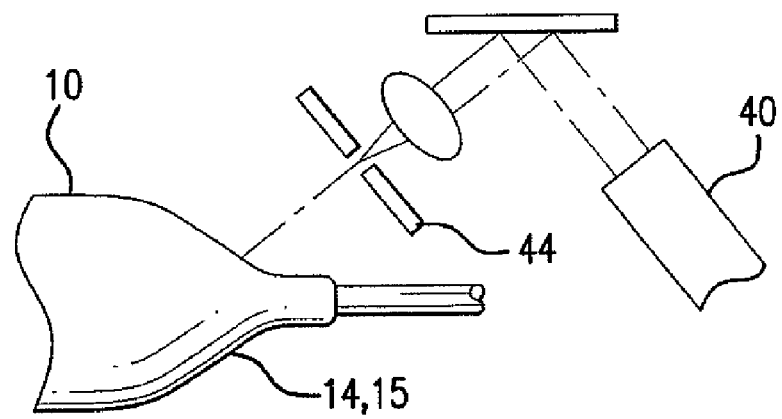
FIG. 10 illustrates a method of forming indentations in balloon material by using a series of mirrors and lenses to direct the laser energy to the balloon surface.

Referring now to FIGS. 9 and 10, there is shown an exemplary embodiment of a method of forming the indentations 24. As noted, the following discussion of the processes of forming the indentations 24 in the cone sections of the balloon is equally applicable to forming the cavities 22 in the proximal or distal sleeve sections of the balloon.

As depicted in FIG. 9, an excimer laser is utilized. As shown in FIG. 9, the head 40 of the excimer laser is positioned so that a beam 42 is approximately perpendicular to the cone section 14, 15 of the balloon 10 where it is desired to form indentations 24 therein. A mask 44 is used to define the location where material will be ablated from the balloon. After a pulse or series of pulses has been emitted by the laser to ablate an indentation or series of indentations as defined by the mask, the balloon may be rotatably indexed to a new position. Another pulse or series of pulses may then be emitted to form a new indentation or series of indentations in the balloon material. This process may be repeated until the desired field of indentations is achieved.

In another aspect of the invention, referring now to FIG. 10, there is shown an alternative method in accordance with the present invention for forming the indentations 24 within the cone sections 14, 15 of the balloon 10. As shown in FIG. 10, a series of lenses and/or mirrors may be used in conjunction with, or without, a mask, to direct the laser beams to the balloon surface, so that the laser and balloon surface can be positioned differently. In addition, a phemto-second laser or any laser capable of material removal may be used in accordance with the methods of the present invention in combination in addition to or as an alternative to the excimer laser.

Figure 11:
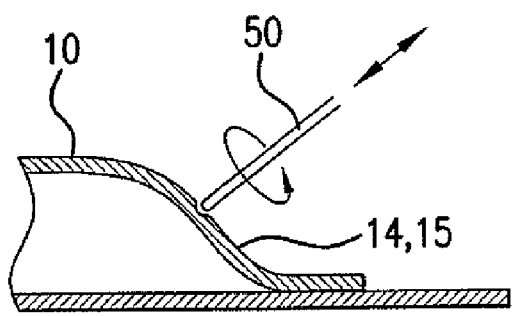
FIG. 11 illustrates a method of forming indentations in balloon material using a mechanical tool such as a grinding tool where indentation depth is controlled by tool displacement.

Referring now to FIG. 11, there is shown yet another method of forming the indentations 24 in the cone section of the balloon 10 in accordance with the present invention. As shown in FIG. 11, the indentations 24 may be formed in the cone section 14, 15 of the balloon 10 through a grinding process. It is contemplated that the grinding process utilized to form the indentations can be embodied in many different manners. For example, one such method is shown in FIG. 11. In accordance with this alternative process the balloon 10 is expanded and fixed to a mandrel. For example, wherein a grinding tool 50 located approximately perpendicular to the balloon surface and is advanced toward the cone sections 14, 15 of the balloon 10. The relative position of the grinding tool and the balloon can then be changed, for example, by rotating the balloon and translating the cutting tool. The process may be repeated to achieve the desired grouping of indentations.

Alternatively, the process may be performed by fixing the grinding tool and displacing the expanded balloon. In addition to using a grinding tool, any other mechanical tool used for removing material may be used, for example but not limited to, drill bits, ultrasonic tools, and fluid jets.

Figure 12:
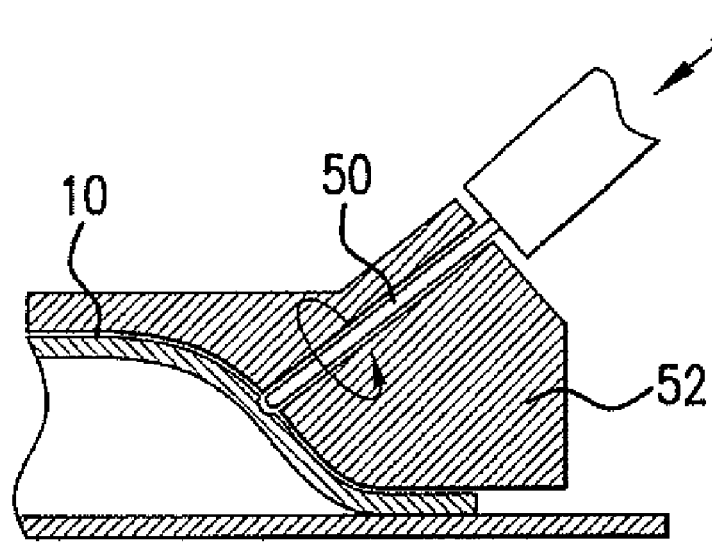
FIG. 12 illustrates a method of forming indentations in balloon material using a mechanical tool and a mechanical stop to limit travel of the grinding tool within the balloon material.

Referring now to FIG. 12, there is illustrated yet another alternative embodiment of a process in accordance with the methods of the present invention. As shown in FIG. 12, the expanded balloon 10 may be pressed against a mask 52. This mask could be, for example, a material shim that has a hole cut in it. The diameter of the hole would closely match the diameter of the tool being used to remove the balloon material. With the mask pressed against the balloon surface on one side, the tool may then be inserted through the mask hole on the other side, moving approximately perpendicular to the balloon surface. The cutting tool would have a stop configured to contact the mask, thereby allowing the tool to plunge only a certain depth into the balloon material. By moving the mask and repeating this process, the desired grouping of indentations may be achieved.

Figure 13:
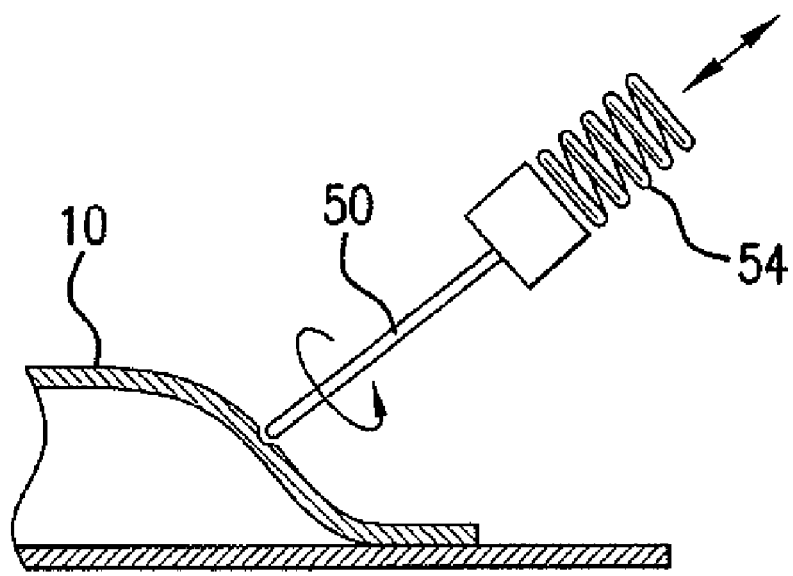
FIG. 13 illustrates a method of forming indentations in balloon material using a mechanical tool and a pressure sensitive mechanism to control travel of the grinding tool with the balloon material.

Referring now to FIG. 13, there is illustrated yet another alternative embodiment of a process in accordance with the methods of the present invention. As shown in FIG. 13 a mechanical tool, such as a grinding tool 50, can be configured to travel approximately perpendicular to the expanded and fixed balloon surface, wherein the mechanical tool further includes a pressure sensitive control feature, such as a spring 54, that permits travel of the cutting tool to only a certain depth. Once the resistance of the cutting surface becomes greater than the force supplied by the spring, then the cutting tool will not remove any more material.

In accordance with the present invention, the ablation may be performed through the use of a laser, such as but not limited to, an excimer laser. For example, a wavelength between 100 and 500 nm may be utilized to form the indentations within the tapered portion 15 of the balloon 10. While other wavelengths (e.g. 248 nm, 308 nm) can yield satisfactory results, the wavelength of 193 nm is best suited for minimizing thermal effects for ablation of a PET dilatation balloon. The fluence level at the surface preferably is in the range of about 100-800 mJ/cm$^2$, and more preferably is about 160 mJ/cm$^2$. The excimer laser beam is pulsed at a repetition rate in the range of about 10-50 pulses per second, with each pulse lasting in the range of about 10-15 ns. Although specific wavelengths, fluence levels and pulse width are given above, these should not be considered limiting in any manner and should be considered only as examples.

Within the operable limits, the fluence, pulse repetition rate, pulse duration and the total number of pulses can be selectively varied to control the nature of excimer laser energy ablation. The polymeric balloon and catheter materials generally have high absorptivity, and thus limit the depth of energy penetration and material removal. For example, the PET balloon material can be removed in ultra thin layers on the order of a micron or a fraction of a micron, depending largely upon the selected fluence. Higher levels of fluence remove greater thicknesses of material, but also tend to increase thermal effects. Pulse duration and pulse frequency can be increased to increase the amount of material removal, although again tending toward thermal effects. Additionally, color may be introduced within or onto the balloon material in order to modify its absorption characteristics and consequently the material removal rate.

Exposure of polymeric materials to laser energy is believed to have photo-chemical and photo-thermal aspects. The former involves the breaking of bonds and disassociation of molecules, leading to momentary pressure increases that eject material, with little or no thermal damage. This effect may be accomplished using a large range of energy wavelengths and laser sources. Photo-thermal effects are the result of molecular vibrational energy. The photo-thermal effects can be minimized by minimizing the energy wavelength (i.e. selecting 193 nm) and by minimizing the fluence. As a result, material is removed essentially without any substantial crystallizing, embrittling or other undesirable altering of the remaining polymeric material. Further as a result of treatment, the wetting characteristics of the polymeric material are changed favorably, so that the surface is more hydrophilic and less thrombogenic.

As described above, there are several approaches to removing material from the tapered sections or sleeve sections of the balloon in accordance with the present invention. Further, the balloon can be supported on a mandrel and inflated. Then, the excimer laser beam can be oriented to the tapered section or the sleeve section, wherein the ablation proceeds in a stepwise process as the ablation occurs, the mandrel and balloon are rotated, and the ablation occurs again. This process is repeated to create a uniform or non-uniform field of indentations or cavities within the respective tapered or sleeve sections of the balloon. Alternatively the balloon may be stationary, while the excimer laser beam is "rotated" with mirrors or other optical components. This process may also include the use of a mask to control the location that laser energy penetrates the balloon material. The use of masks can increase the efficiency of the material removal process.

Yet another alternative involves positioning the evacuated balloon against a plate in a flattened orientation, prior to its bonding to the catheter. Then, the excimer laser beam can be traversed across the desired balloon sections, incrementally creating indentations. This is preferably accomplished through the use of a mask to control the location that laser energy penetrates the balloon material. After ablation of one side, the balloon is turned over and the reverse side is ablated.

The catheter shaft may also be ablated at other locations, e.g. at the distal section or distal tip, the balloon sleeve that extends beyond the distal cone of the dilatation balloon may be ablated. Ablating indentations in the catheter can improve trackability in terms of negotiating sharp turns in vascular passages.

Alternatively, material may be selectively removed through the use of different laser sources. For examples, but not limited to, a phemto-second laser. Similar to the use of ablative excimer laser, the laser itself or the work piece may be moved relative to the other. By doing this, and by controlling the activity of the laser, a plurality of indentations can be formed in the balloon and catheter sections.

Indentations within the balloon and catheter sections or cavities within the sleeve sections of the balloon may also be achieved through the use of mechanical ablation methods. For example, processes such as drilling, milling, or grinding can be used to locally remove material in the desired areas. There are several methods of using these types of processes to achieve the goal of this invention. For example, a grinding or drilling tool may be pressed against the balloon or catheter while the tool is being rotated. The depth of material removal can be determined by displacement of the cutter or the cutting piece. The depth of material removal can also be determined by supporting either the cutter, and then pressing the tapered portion of the balloon piece against the support piece using a pressure sensitive mechanism that controls the depth of the indentation. The pressure sensitive mechanism can be, for example, a spring or pneumatic cylinder that is adjusted to provide a given depth of material removal. Additionally, using a pressure sensitive mechanism, the time of contact may be varied to control the depth of the indentation. Additionally, a cutting tool can extend a certain distance from the surface of a retaining feature. The balloon may then be inflated or pressed against the retaining feature, thereby forming an indentation with a depth approximately equal to the extension distance of the cutting tool from the retaining feature surface. A combination of these processes, or a process obvious to those skilled in the art, may also be used to create this invention.

Another means of creating the desired grouping of indentations or cavities is to deflate the balloon and secure it against a support, for example a plate. Any of the variety of means for removing material such as described above may then be employed to create the desired grouping of indentations.

In another aspect of the invention, the balloon can be fabricated from a tubular member such as a polymer tubular member. In this manner, the at least one cavity and/or the at least one indentation can be formed in a section of the tubular member that corresponds to the sleeve sections and/or the cone sections of a balloon when formed from the tubular member. In this regard, predetermined sites of the tubular member which correspond to the distal and proximal sleeve sections and/or the distal and proximal cone sections are determined. The at least one cavity and/or the at least one indentations is formed in the sleeve and/or cone sections, respectively. Thereafter, the tubular member is processed according to methods known in the art to form a balloon having at least one cavity formed in the proximal and/or distal sleeve sections. If desired, the at least one indentation can be formed in the proximal and/or distal cone sections.

The balloon of the present invention may be disposed on different types of shafts, or on multiple shafts. For example, the invention may include a balloon disposed on a fixed wire device.

In accordance with another aspect of the invention, a method for forming a compliant medical device is provided. The method comprises providing a balloon formed from polymeric material. A portion of polymeric material is removed from the sleeve sections of the balloon to define at least one cavity and preferably a plurality of cavities along a length thereof, as discussed above. The balloon is configured about a catheter shaft, preferably the distal section of the catheter shaft. The balloon is secured to the catheter shaft by bonding the proximal and distal sleeve sections to the outer surface of the catheter shaft such that during the bonding step the polymeric material of the sleeve sections becomes molten, for example by the application of heat or other energy source. The molten polymer flows into the cavities defined in the sleeve sections to achieve a reduced profile bonding area.

The reduced profile bonding area is defined by at least a portion of the balloon polymeric material flowing into at least one cavity. The method may further include the step of removing a portion of material from the cone sections of the balloon to define indentations along a length thereof as discussed above.

Those skilled in the art may recognize other equivalents to the specific embodiments described herein which equivalents are intended to be encompassed by the claims attached hereto.

What is claimed is:

1. A method for forming a compliant medical device, comprising:
   providing a balloon formed from polymeric material, the balloon having
      a proximal cone section, distal cone section, a medial section disposed therebetween;
      a proximal sleeve section disposed proximal the proximal cone section and a distal sleeve section disposed distal the distal cone section, the proximal and distal sleeve sections each having a wall with an inner surface, an outer surface and a thickness defined therebetween;
   removing a portion of polymeric material from the inner surface of the wall of at least one of the proximal or distal sleeve section to a depth less than the thickness of the wall without penetrating the outer surface of the wall;
   positioning the balloon about a portion of a catheter shaft;
   bonding the at least one of the proximal or distal sleeve section to the portion of the catheter shaft to define a reduced profile bonding area.

2. The method of claim 1, wherein the polymeric material is removed from the wall of the proximal sleeve section.

3. The method of claim 1, wherein the polymeric material is removed from the wall of the distal sleeve section.

4. The method of claim 1, wherein the polymeric material is removed from the wall of the proximal sleeve section and from the wall of the distal sleeve section.

5. The method of claim 1, wherein removing the polymeric material includes milling the wall of the at least one of the proximal or distal sleeve section.

6. The method of claim 1, wherein removing the polymeric material includes at least one technique selected from the group consisting of laser ablation, mechanical grinding, drilling, chemical or mechanical etching and any combination thereof.

7. The method of claim 1, wherein removing the polymeric material includes cutting circumferentially about the at least one of the proximal or distal sleeve section.

8. The method of claim 1, wherein removing the polymeric material includes cutting spirally about the at least one of the proximal or distal sleeve section.

9. The method of claim 7, wherein the polymeric material is removed at a generally constant depth from the inner surface along a length of the at least one of the proximal or distal sleeve section.

10. The method of claim 7, wherein the polymeric material is removed at a varied depth from the inner surface along a length of the at least one of the proximal or distal sleeve section.

11. The method of claim 1 wherein the at least one of the proximal or distal sleeve section further includes an edge, and wherein the polymeric material is removed from the inner surface along a longitudinal length from the edge.

12. The method of claim 1, wherein the at least one of the proximal or distal sleeve section has a length and wherein the polymeric material is removed along the entire length.

13. The method of claim 1, wherein bonding includes heat welding the at least one of the proximal and distal sleeve section to the catheter shaft.

14. The method of claim 1, wherein the catheter shaft includes an inner member and an outer member and wherein bonding comprises bonding the proximal sleeve section to the outer member and the distal sleeve section to the inner member.

15. The method of claim 1, further including removing a portion of polymeric material from the at least one of the proximal or distal cone sections to define at least one indentation along a length thereof.

16. The method of claim 15, wherein the at least one of the proximal or distal cone section includes a wall having a first thickness, the medial section includes a wall having a second thickness, and the at least one indentation includes a depth extending into the wall of the proximal or distal cone defines a third reduced thickness along a section of the wall of the at least one of the proximal or distal cone section.

17. The method of claim 16, wherein the third reduced thickness is substantially equal to the second thickness.

18. The method of claim 16, wherein the third reduced thickness is greater than or equal to the second thickness.

19. The method of claim 15, wherein removing material from the at least one of the proximal or distal cone section is performed by at least one technique selected from the group consisting of laser ablation, mechanical grinding, milling, blasting, drilling, chemical or mechanical etching and any combination thereof.

* * * * *